(12) United States Patent  
Song

(10) Patent No.: US 10,265,052 B2
(45) Date of Patent: Apr. 23, 2019

(54) METHOD OF DISPLAYING ULTRASOUND IMAGE AND ULTRASOUND DIAGNOSIS APPARATUS

(71) Applicant: SAMSUNG MEDISON CO., LTD., Hongcheon-gun (KR)

(72) Inventor: Min-jung Song, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 7 days.

(21) Appl. No.: 15/497,911

(22) Filed: Apr. 26, 2017

(65) Prior Publication Data

US 2017/0325781 A1 Nov. 16, 2017

Related U.S. Application Data

(60) Provisional application No. 62/333,961, filed on May 10, 2016.

(30) Foreign Application Priority Data

Jul. 26, 2016 (KR) .................. 10-2016-0094819

(51) Int. Cl.
*G06F 19/00* (2018.01)
*A61B 8/00* (2006.01)
(Continued)

(52) U.S. Cl.
CPC ............ *A61B 8/465* (2013.01); *A61B 8/0883* (2013.01); *A61B 8/14* (2013.01); *A61B 8/4405* (2013.01);
(Continued)

(58) Field of Classification Search
CPC .. G06F 17/211; G06F 17/212; G06F 17/2247; G06F 17/30056; G06F 17/241;
(Continued)

(56) References Cited

U.S. PATENT DOCUMENTS 6,289,239 B1* 9/2001 Panescu ............... A61B 5/0422
600/523
8,659,507 B2* 2/2014 Roncalez ............ G06F 3/04847
345/173
(Continued)

FOREIGN PATENT DOCUMENTS

EP 2 821 014 A1 1/2015
JP 2013182442 A 9/2013
(Continued)

OTHER PUBLICATIONS

Communication dated Sep. 27, 2017, issued by the European Patent Office in counterpart European Application No. 17169001.9.

*Primary Examiner* — Scott T Baderman
*Assistant Examiner* — Hassan Mrabi
(74) *Attorney, Agent, or Firm* — Sughrue Mion, PLLC

(57) ABSTRACT

A method of displaying an ultrasound image includes: displaying an ultrasound image representing an object; generating a first text and a plurality of icons representing information about a region of interest included in the object; displaying the first text and the plurality of icons on the ultrasound image; generating at least one second text when a first icon is selected from among the plurality of icons; and displaying the at least one second text on a region relating to information represented by the at least one second text.

19 Claims, 15 Drawing Sheets

(51) Int. Cl.
*A61B 8/08* (2006.01)
*G16H 50/20* (2018.01)
*A61B 8/14* (2006.01)
*G06F 17/24* (2006.01)
*G06T 11/60* (2006.01)
*G06F 3/0481* (2013.01)
*G06F 3/0482* (2013.01)

(52) U.S. Cl.
CPC .......... *A61B 8/4427* (2013.01); *A61B 8/4472* (2013.01); *A61B 8/463* (2013.01); *A61B 8/464* (2013.01); *A61B 8/467* (2013.01); *G06F 17/241* (2013.01); *G06F 19/00* (2013.01); *G06F 19/321* (2013.01); *G06T 11/60* (2013.01); *G16H 50/20* (2018.01); *G06F 3/0482* (2013.01); *G06F 3/04817* (2013.01); *G06T 2200/24* (2013.01); *G06T 2210/41* (2013.01)

(58) Field of Classification Search
CPC .... G06F 19/321; G06F 19/00; G06F 3/04817; G06F 3/0482; A61B 8/465; A61B 8/0883; A61B 8/4405; A61B 8/4427; A61B 8/4472; A61B 8/464; A61B 8/467; A61B 8/14; A61B 8/463; G16H 50/20; G06T 11/60; G06T 2200/24; G06T 2210/41

USPC .......................................................... 715/202
See application file for complete search history.

(56) References Cited

U.S. PATENT DOCUMENTS

| | | | | |
|---|---|---|---|---|
| 8,747,322 | B2* | 6/2014 | Kim | A61B 8/00 600/443 |
| 9,552,153 | B2* | 1/2017 | Lee | G06F 3/04883 |
| 2013/0072795 | A1* | 3/2013 | Mo | A61B 8/465 600/443 |
| 2013/0326386 | A1* | 12/2013 | Vendrell | G06F 19/321 715/771 |
| 2014/0181716 | A1 | 6/2014 | Merritt et al. | |
| 2014/0316271 | A1* | 10/2014 | Hyun | A61B 8/12 600/443 |
| 2015/0141823 | A1 | 5/2015 | Lee et al. | |
| 2015/0164474 | A1 | 6/2015 | Lee et al. | |
| 2016/0242732 | A1* | 8/2016 | Strassner | A61B 8/02 |

FOREIGN PATENT DOCUMENTS

| | | |
|---|---|---|
| JP | 2014-233468 A | 12/2014 |
| KR | 1020110094562 A | 8/2011 |
| KR | 1020120063407 A | 6/2012 |
| KR | 1020140025048 A | 3/2014 |
| WO | 2009/049363 A1 | 4/2009 |

* cited by examiner

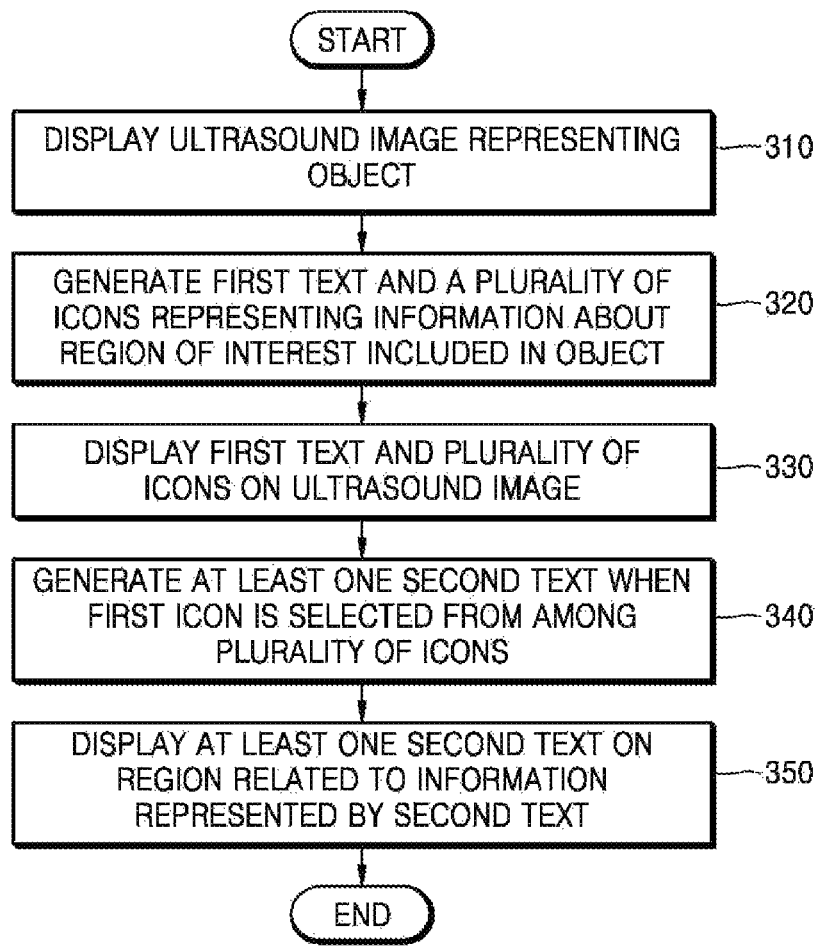

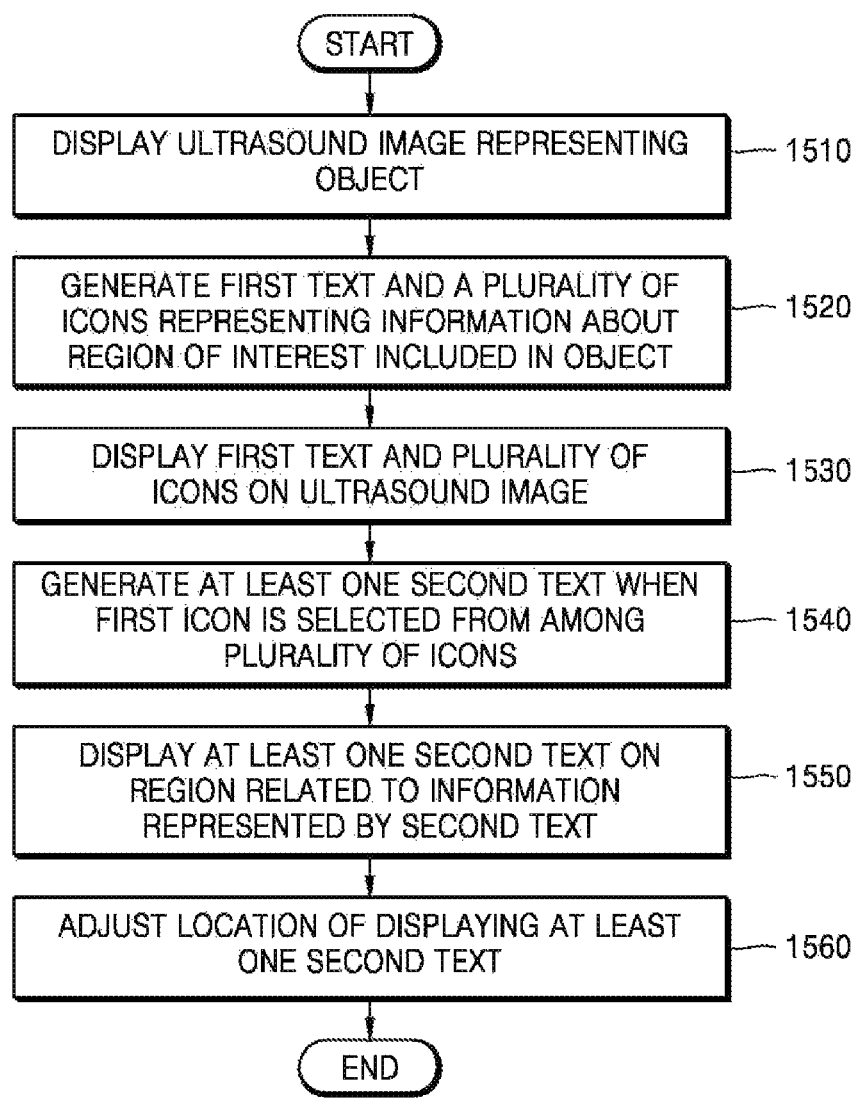

METHOD OF DISPLAYING ULTRASOUND IMAGE AND ULTRASOUND DIAGNOSIS APPARATUS

CROSS-REFERENCE TO RELATED APPLICATIONS

This application claims the benefit of U.S. Provisional Application No. 62/333,961, filed on May 10, 2016, in the US Patent Office and Korean Patent Application No. 10-2016-0094819, filed on Jul. 26, 2016, in the Korean Intellectual Property Office, the disclosures of which are incorporated herein in their entireties by reference.

BACKGROUND

1. Field

The present disclosure relates to methods of displaying an ultrasound image and ultrasound diagnosis apparatuses.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow).

SUMMARY

Provided are methods of displaying an ultrasound image and ultrasound diagnosis apparatuses.

Provided are non-transitory computer-readable recording media having recorded thereon a program, which when executed by a computer, performs the above methods.

Additional aspects will be set forth in part in the description which follows and, in part, will be apparent from the description, or may be learned by practice of the presented embodiments.

According to an aspect of an embodiment, a method of outputting an ultrasound image, the method including: displaying an ultrasound image representing an object; generating a first text and a plurality of icons representing information about a region of interest included in the object; displaying the first text and the plurality of icons on the ultrasound image; generating at least one second text when a first icon is selected from among the plurality of icons; and displaying the at least one second text on a region relating to information represented by the at least one second text.

According to an aspect of another embodiment, a non-transitory computer-readable recording medium has recorded thereon a program, which when executed by a computer, performs the above method.

According to an aspect of another embodiment, an ultrasound diagnosis apparatus including: a probe configured to irradiate ultrasound signals to an object and to receive echo signals corresponding to the ultrasound signals; a controller configured to generate a first text and a plurality of icons representing information about a region of interest included in the object, and to generate at least one second text when a first icon is selected from among the plurality of icons; and a display configured to display the first text and the plurality of icons on an ultrasound image, and to display the at least one second text on a region relating to information represented by the at least one second text.

BRIEF DESCRIPTION OF THE DRAWINGS

These and/or other aspects will become apparent and more readily appreciated from the following description of the embodiments, taken in conjunction with the accompanying drawings in which:

FIG. 3 is a flowchart illustrating an example of a method of displaying an ultrasound image, according to an embodiment;

FIG. 15 is a flowchart illustrating another example of a method of displaying an ultrasound image, according to an embodiment.

DETAILED DESCRIPTION

Figure 1:
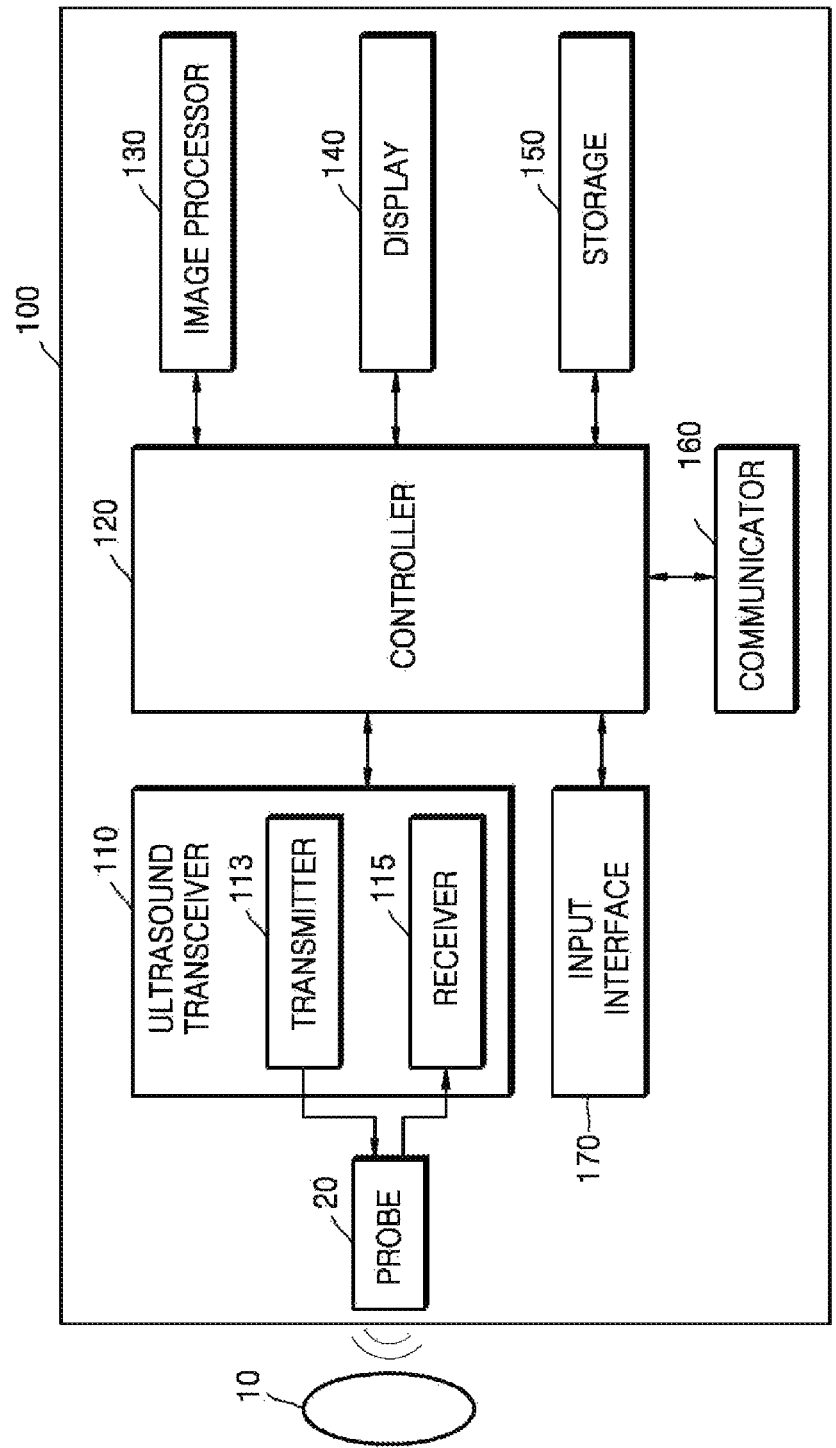
FIG. 1 is a block diagram of an ultrasound diagnosis apparatus according to an embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
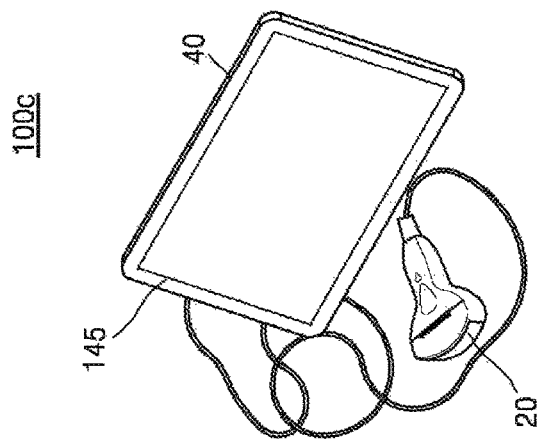
FIGS. 2A to 2C are diagrams of an ultrasound diagnosis apparatus according to an embodiment.
Figure 2B:
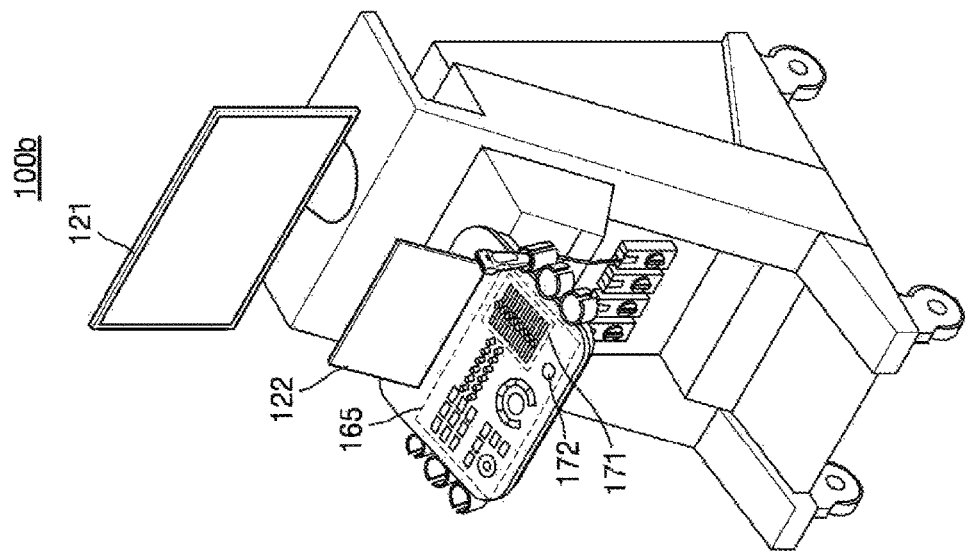
Figure 2A:
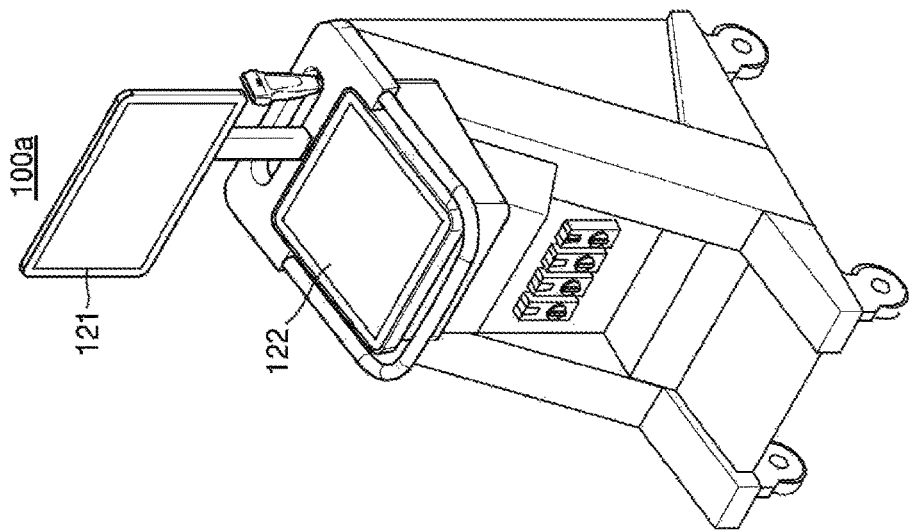

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

FIG. 3 is a flowchart illustrating an example of a method of displaying an ultrasound image, according to an embodiment.

Referring to FIG. 3, the method of displaying an ultrasound image consists of processes that are performed in a time-serial manner in the ultrasound diagnosis apparatus 100, 100a, 100b, or 100c illustrated in FIG. 1 and FIGS. 2A to 2C. Therefore, although omitted hereinafter, descriptions about the ultrasound diagnosis apparatus 100, 100a, 100b, or 100c illustrated in FIGS. 1 and 2A to 2C provided above are also applied to the method of displaying the ultrasound image illustrated with reference to FIG. 3.

In operation 310, a display 140 displays an ultrasound image representing an object. In detail, an image processor 130 generates an ultrasound image by using ultrasound data generated by an ultrasound receiver 115. In addition, the display 140 displays the ultrasound image generated by the image processor 130 on a screen.

In operation 320, a controller 120 generates a first text and a plurality of icons representing information about a region of interest (ROI) included in the object. Here, the region of interest may denote a partial region of the object, that a user is interested in. For example, when it is assumed that the object is the heart, the region of interest may be an atrium, a ventricle, a vein, or an artery in the heart.

The first text denotes a word or a phrase displayed on the ultrasound image. For example, the user may input information about the region of interest as a text onto the ultrasound image via an input unit 170, or may select one of texts that are stored in advance. The controller 120 generates the text input or selected by the user as the first text.

If the user selects the first text from among the texts stored in advance, the controller 120 analyzes the ultrasound image to obtain information about the region of interest. For example, the controller 120 segments a shape shown in the ultrasound image, and compares the segmented shape with shapes stored in advance to identify which organ (or which part of an organ) the object and/or the region of interest is. In addition, the controller 120 selects the first text from among the texts stored in advance, based on the information about the region of interest. For example, the controller 120 may select the first text from among the texts stored in advance, according to which organ (or which part of an organ) the region of interest relates. Hereinafter, an example of the first text will be described with reference to FIG. 4.

Figure 4:
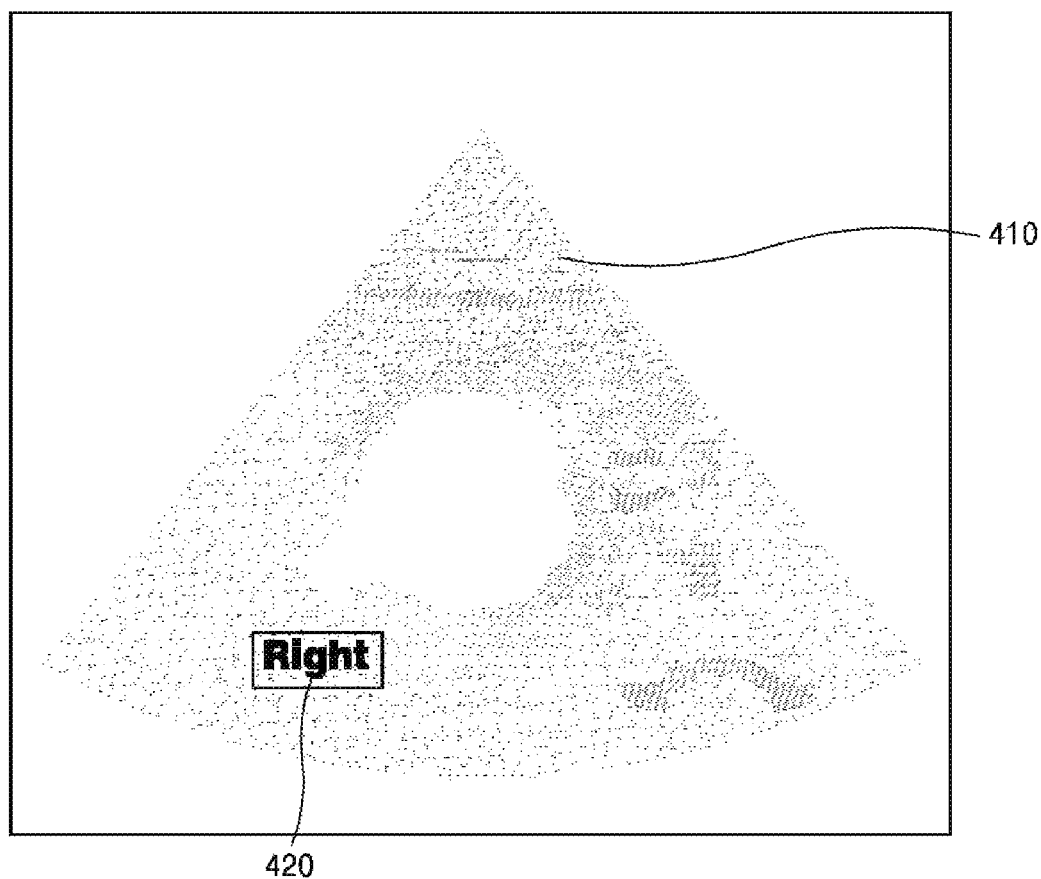
FIG. 4 is a diagram showing an example of a first text according to an embodiment.

FIG. 4 is a diagram showing an example of a first text according to an embodiment.

Referring to FIG. 4, the display 140 may display an ultrasound image 410 on a screen. If there is no information (e.g., text) about the ultrasound image 410 written on the ultrasound image 410, it may be difficult to identify which organ the object (or the region of interest) on the ultrasound image 410 is or how the state of the object (or the region of interest) is. That is, in a case where additional information (e.g., text) is written on the ultrasound image 410, the user may easily identify the ultrasound image 410.

For example, the user may input a first text 420 to be represented on the ultrasound image 410 via the input unit 170. As another example, the user may select one of texts stored in advance as the first text 420 via the input unit 170. If the user selects one of the texts stored in advance as the first text 420, the display 140 may display a list of the stored texts on the screen and the user may select the first text 420 from the list displayed on the screen. Here, if there are many texts that are stored in advance, the ultrasound image 410 may be covered when the list of the texts stored in advance is displayed on the screen. In addition, it may not be easy for the user to find the first text 420 from the list displayed on the screen.

As will be described later, the controller 120 may generate a plurality of icons, as well as the first text 420, and the display 140 may display the plurality of icons on the ultrasound image 410 with the first text 420. Therefore, the user may easily and conveniently select the first text 420 from among the texts stored in advance.

Referring back to FIG. 3, in operation 320, the controller 120 may generate the first text representing information about the region of interest included in the object and the plurality of icons. Here, each of the plurality of icons may denote an indicator that stands for a group of texts stored in advance. For example, the plurality of icons may include icons representing names of the organs related to the region of interest, icons representing terminologies related to the first text, icons representing medical terms, and icons representing various directions.

In operation 330, the display 140 may display the first text and the plurality of icons on the ultrasound image. For example, the display 140 may display the plurality of icons to be adjacent to the first text. If the display 140 displays the first text within a polygonal frame (e.g., a square), the plurality of icons may be displayed adjacent to sides of the polygon.

Hereinafter, an example of displaying the first text and the plurality of icons will be described below with reference to FIG. 5.

Figure 5:
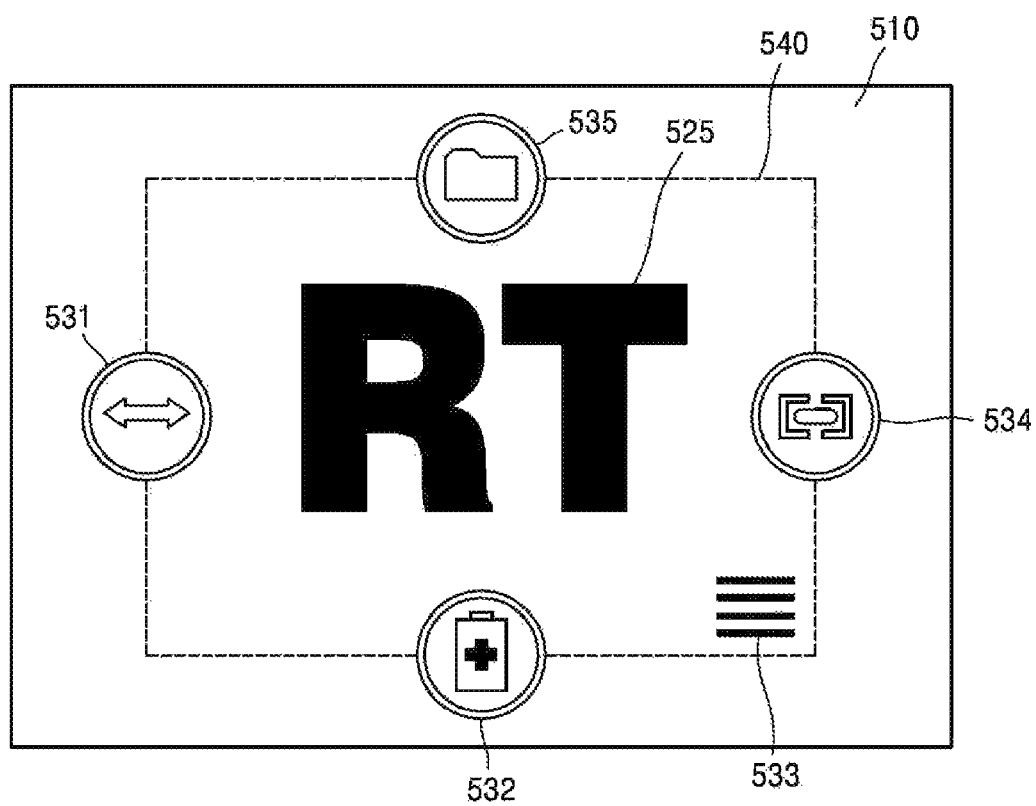
FIG. 5 is a diagram illustrating an example of displaying a first text and a plurality of icons, according to an embodiment.

FIG. 5 is a diagram illustrating an example of displaying a first text and a plurality of icons, according to an embodiment.

FIG. 5 shows an example of displaying a first text 520 and a plurality of icons 531, 532, 533, 534, and 535 on an ultrasound image 510.

The controller 120 generates the first text 520 representing information about the region of interest, and the display 140 displays the first text 520 on the ultrasound image 510. For example, the controller 120 may generate the first text 520 based on the information input through the input unit 170. The information input through the input unit 170 may include a text input by the user or a text selected by the user from among the texts stored in advance. Otherwise, the controller 120 may obtain information about the region of interest shown in the ultrasound image 510, and may select the first text 510 from among the texts stored in advance based on the information.

The controller 120 generates the plurality of icons 531, 532, 533, 534, and 535, and the display 140 displays the plurality of icons 531, 532, 533, 534, and 535 on the ultrasound image 510. Here, the plurality of icons 531, 532, 533, 534, and 535 may be displayed adjacent to sides of a polygon 540 including the first text 520. For example, when it is assumed that the polygon 540 is a rectangle as shown in FIG. 5, each of the plurality of icons 531, 532, 533, 534, and 535 may be displayed at four sides of the rectangle 540 or adjacent to the rectangle 540.

The plurality of icons 531, 532, 533, 534, and 535 may include the icon 531 representing directions, the icon 532 representing medical terms, the icon 533 representing the list of the texts stored in advance, the icon 534 representing the terminologies regarding the first text, and the icon 535 representing name of the organ relating to the region of interest. However, things the plurality of icons 531, 532, 533, 534, and 535 shown in FIG. 5 stand for are not limited to the above examples, and each of the plurality of icons 531, 532, 533, 534, and 535 may be an icon representing texts grouped based on various criteria.

For example, the icon 531 representing directions may stand for terminologies representing directions such as left, right, up, and down. In addition, the icon 532 representing the medical terms may stand for the medical terms such as common bile duct (CBD) or inferior vena cava (IVC). In addition, the icon 533 representing the list of the texts stored in advance may stand for the list including all texts stored in the ultrasound diagnosis apparatus 100, 100a, 100b, or 100c in advance. Also, the icon 534 representing the terminologies regarding the first text may stand for terminologies used in relation to the first text. In addition, the icon 535 representing the name of the organ relating to the region of interest may stand for texts such as the right ventricle, the left atrium, and the left ventricle, when it is assumed that the region of interest is the right atrium of the heart.

Referring back to FIG. 3, in operation 340, when the user selects a first icon from among the plurality of icons, the controller 120 may generate at least one second text. For example, the user may select one (first icon) of the plurality of icons displayed on the screen, the controller 120 may generate at least one second text corresponding to the first icon selected by the user.

According to the above description with reference to operation 320, each of the plurality of icons denotes an indicator representing a group of texts stored in advance.

That is, the texts stored in advance may be grouped based on a predetermined criterion, and a group may be mapped with each of the plurality of icons. Therefore, when the user selects the first icon, the controller 120 identifies the group mapped with the first icon and selects the second text included in the identified group.

If the user selects the first icon once when there are a plurality of texts included in the identified group, the controller 120 may select a text that is most frequently used, as the second text. Otherwise, if the user selects the first icon a plurality of times, the controller 120 may sequentially generate second texts that are different from one another. For example, the controller 120 may select texts in an order of utilization frequency from among the plurality of texts included in the group, and may determine the selected texts as the second texts.

In operation 350, the display 140 may display at least one second text on a region related to the information represented by the second text. For example, the display 140 may display the at least one second text adjacent to sides of a polygon including the first text.

As an example, the display 140 may display the second text adjacent to a corner that is located at a side represented by the second text based on the first text, from among the sides of the polygon including the first text. For example, when it is assumed that the second text denotes 'left' and the polygon including the first text is a rectangle, the display 140 may display the second text to be adjacent to a left corner of the rectangle.

As another example, the display 140 may display the second text at a location represented by the second text in the ultrasound image. For example, when it is assumed that the ultrasound image is an image of the heart and the second text denotes the 'right atrium', the display 140 may display the second text at a region where the right atrium is expressed in the ultrasound image.

Hereinafter, examples of displaying the ultrasound image by the ultrasound diagnosis apparatus 100, 100a, 100b, or 100c will be described in detail below with reference to FIGS. 6 to 14.

Figure 6:
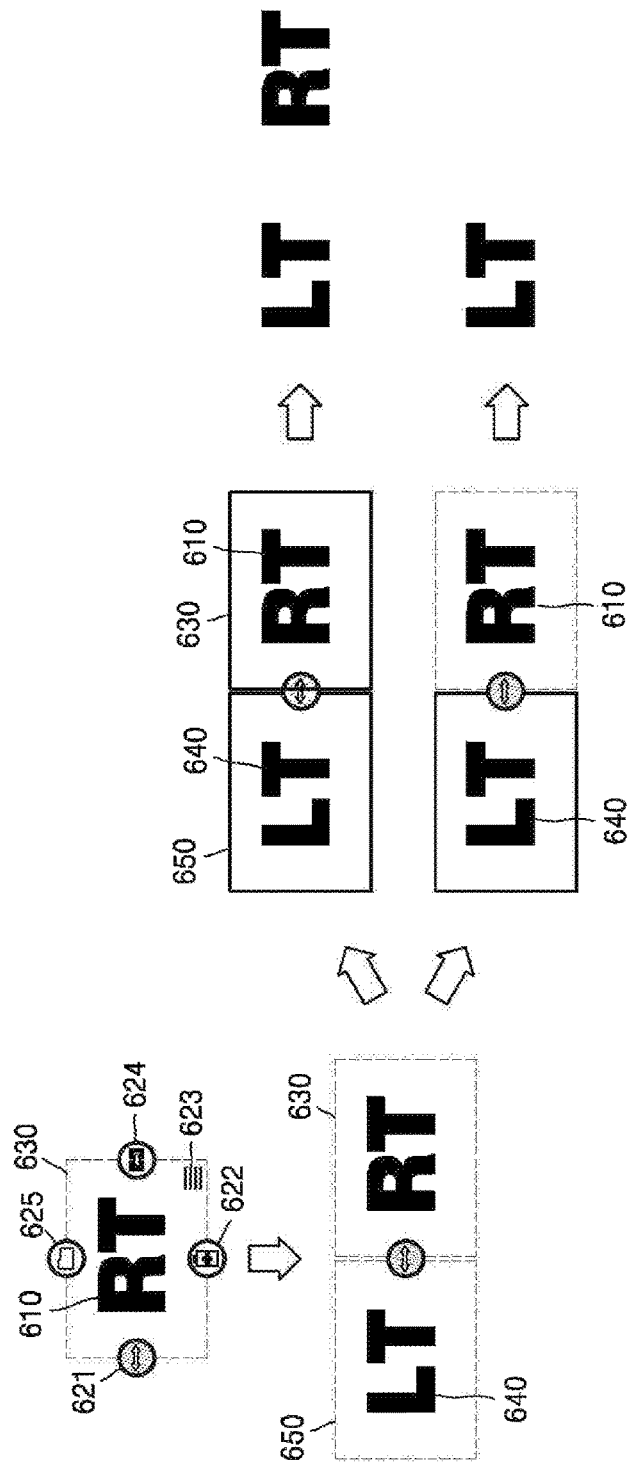
FIG. 6 is a diagram illustrating an example of displaying a first text and a second text, according to an embodiment.

FIG. 6 is a diagram illustrating an example of displaying a first text and a second text, according to an embodiment.

Referring to FIG. 6, the user may select a first icon 621 from among a plurality of icons 621, 622, 623, 624, and 625 displayed with a first text 610. When the user selects the first icon 621, the controller 120 generates a second text 640. For example, when it is assumed that the first icon 621 denotes various directions and the first text 610 denotes a right side (RT), the controller 120 may generate a text 'LT' representing the left side as the second text 640.

The display 140 may display the second text 640 to be adjacent to a side of a polygon 630 including the first text 610. The display 140 may display the second text 640 to be adjacent to the corner located at the direction represented by the second text 640 based on the location of the first text 610, from among the sides of the polygon 630. For example, when it is assumed that the first text 610 denotes the right side (RT) and the second text 640 denotes the left side (LT), the display 140 may display the second text 640 to be adjacent to the left corner of the polygon 630. Here, the display 140 may output a predetermined polygon 650 along with an outskirt of the second text 640.

In a state where the first text 610 and the second text 640 are output, the user may select at least one of the first and second texts 610 and 640. For example, the user may select both the first text 610 and the second text 640 via the input unit 170, or may select the second text 640. When the user finishes the selection, the display 140 may display the selected text to be distinguished from the unselected text. For example, if the second text 640 is selected, the display 140 may express the polygon 650 in solid lines and express the polygon 630 in dashed lines. However, the example of displaying the text selected by the user to be distinguished from the unselected text on the display 140 is not limited to the above example.

After that, the display 140 deletes the unselected text from the screen. For example, when the user selects both the first text 610 and the second text 640, the display 140 may continuously display the first text 610 and the second text 640 on the screen. On the other hand, when the user selects the second text 640, the display 140 deletes the first text 610 from the screen.

Figure 7:
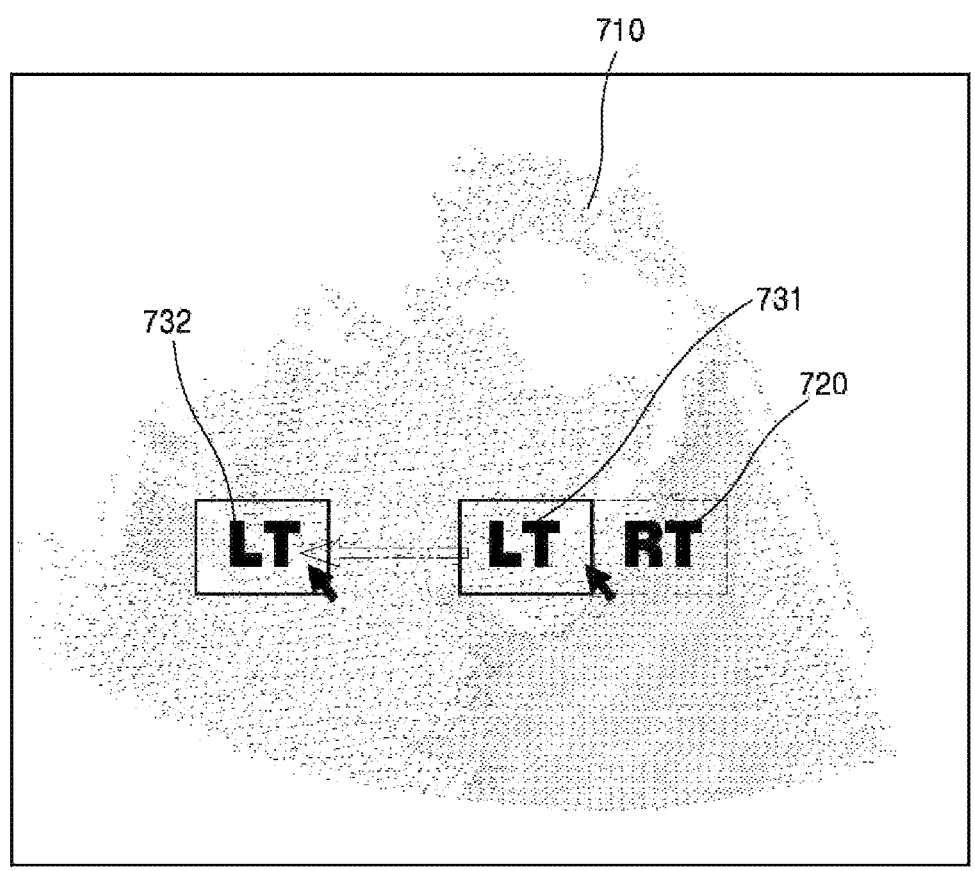
FIG. 7 is a diagram illustrating an example of displaying a first text and a second text together with an ultrasound image, according to an embodiment.

FIG. 7 is a diagram illustrating an example of displaying a first text 720 and a second text 731 together with an ultrasound image 710, according to an embodiment.

Referring to FIG. 7, the first text 720 and the second text 731 are displayed on the ultrasound image 710. Here, the example of displaying the first text 720 and the second text 731 is the same as the above description provided with reference to FIG. 6.

In addition, the display 140 may adjust a location of displaying the second text 731. For example, when the user adjusts the location of the second text 731 displayed on the screen via the input unit 170, the display 140 may display a second text 732 at an adjusted location.

Figure 8:
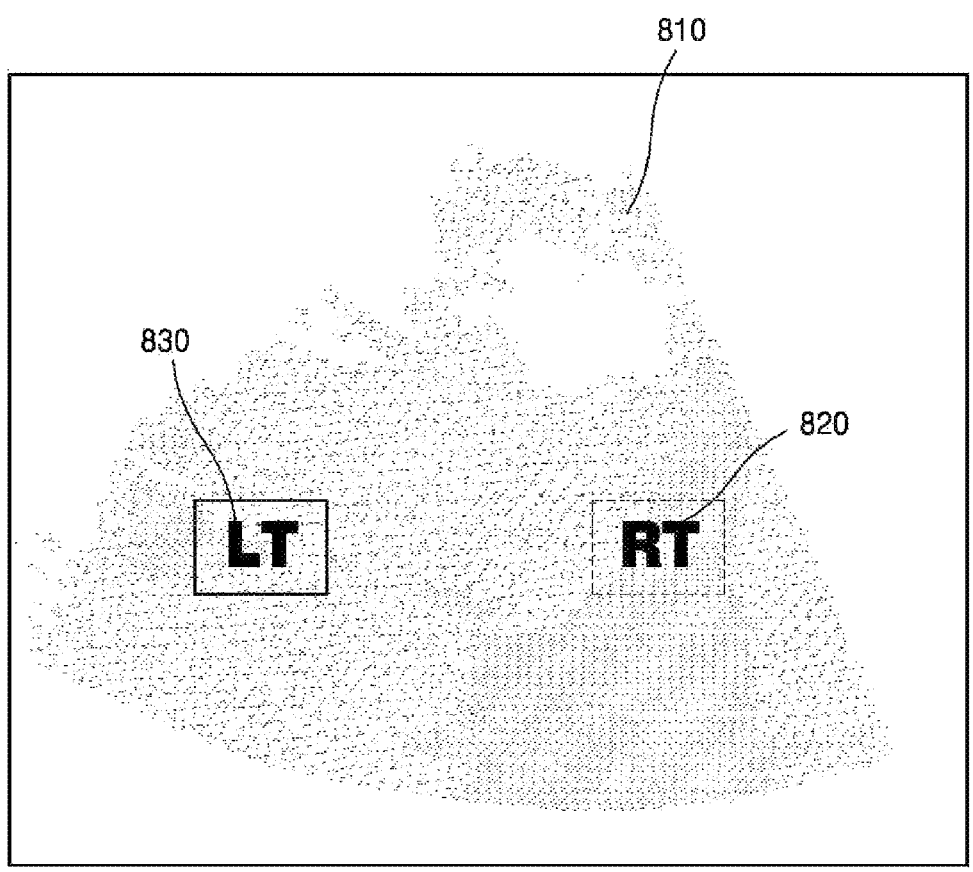
FIG. 8 is a diagram illustrating another example of displaying a first text and a second text together with an ultrasound image, according to an embodiment.

FIG. 8 is a diagram illustrating another example of displaying a first text 820 and a second text 830 together with an ultrasound image 810, according to an embodiment.

Referring to FIG. 8, the first text 820 and the second text 830 are displayed on the ultrasound image 810. Here, the example of displaying the first text 820 and the second text 830 is the same as the above description provided with reference to FIG. 6.

In addition, the display 140 may display the second text 830 at a location represented by the second text 830 on the ultrasound image 810. When being compared with FIG. 7, the second text 731 of FIG. 7 is displayed adjacent to the first text 720. On the other hand, the second text 830 of FIG. 8 is not adjacent to the first text 820, but is displayed away from the location of displaying the first text 820.

For example, the controller 120 may identify the meaning of the second text 830 and the object shown in the ultrasound image 810. In addition, the controller 120 identifies the location represented by the meaning of the second text 820 in the ultrasound image 810, and the display 140 may display the second text 830 on the identified location. In addition, the display 140 may adjust the location of displaying the second text 830 based on the user input, as described above with reference to FIG. 7.

Figure 9:
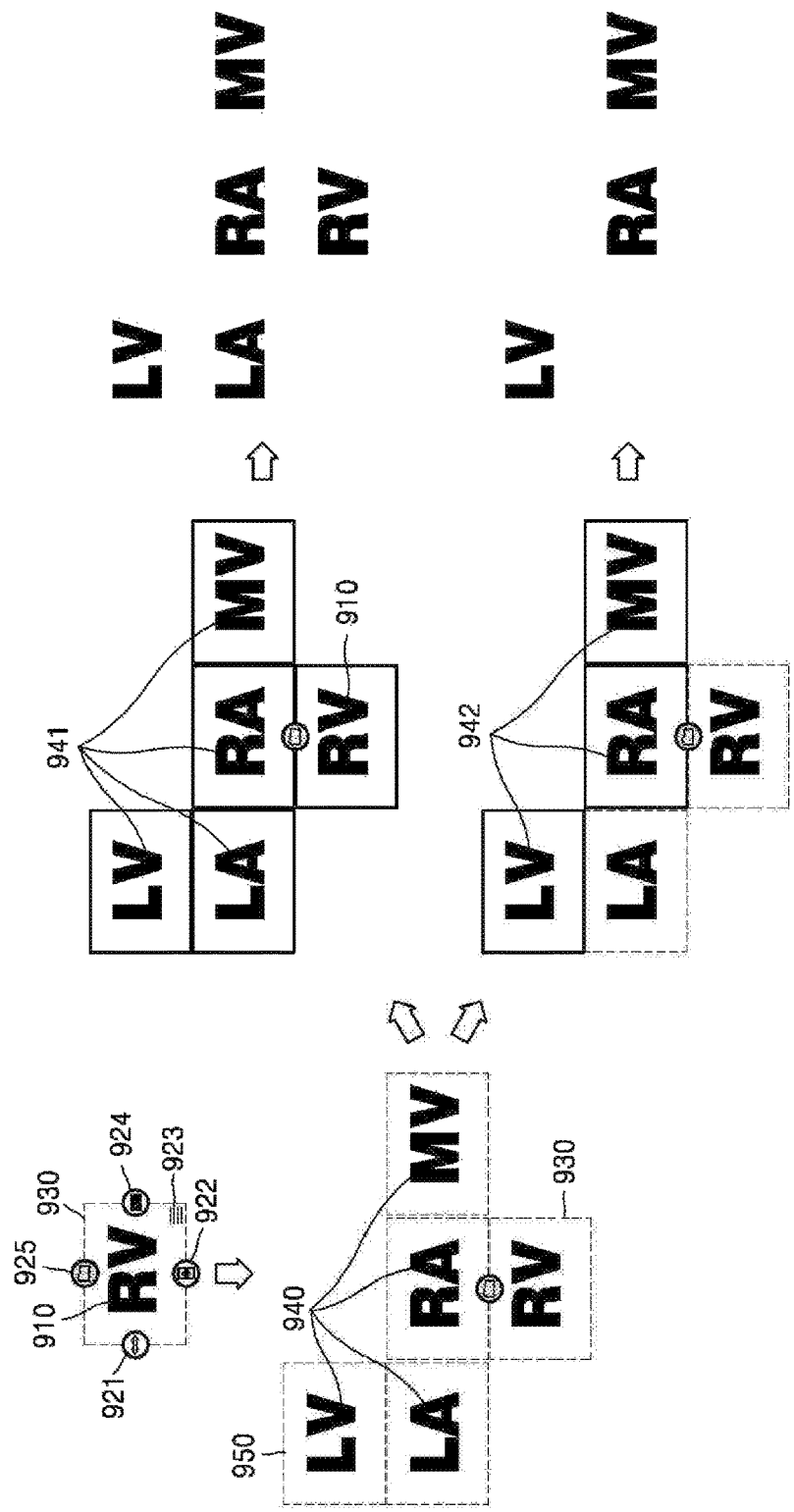
FIG. 9 is a diagram illustrating another example of displaying a first text and a second text, according to an embodiment.

FIG. 9 is a diagram illustrating another example of displaying a first text 910 and a second text 940, according to an embodiment.

Referring to FIG. 9, the user may select a second icon 925 from among a plurality of icons 921, 922, 923, 924, and 925 displayed with the first text 910. When the user selects the second icon 925, the controller 120 generates second text 940. For example, when it is assumed that the second icon 925 stands for the name of the organ relating to the region of interest and the first text 910 is 'RV', the controller 120 may generate LV, MV, LA, RA, etc. as the second texts 940.

The display 140 may display the second texts 940 to be adjacent to sides of a polygon 930 including the first text 910. The display 140 may display the second texts 940 to be adjacent to the sides located at the directions represented respectively by the second texts 940 based on the location of the first text 910, from among the sides of the polygon 930. Here, the display 140 may output a predetermined polygon 950 along with an outskirt of each of the second texts 940.

In a state where the first text 910 and the second texts 940 are output, the user may select at least one of the first and second texts 910 and 940. For example, the user may select all of the first text 910 and the second texts 940 via the input unit 170, or may select at least one of the second texts 940. When the user finishes the selection, the display 140 may display the selected text to be distinguished from the unselected text. For example, if all of the first and second texts 910 and 940 are selected, the display 140 may represent all of the polygons surrounding the first text 910 and the second texts 940 in the solid lines. On the other hand, if some of the second texts 940 is only selected, the polygons surrounding the selected second texts may be represented in the solid lines and the polygons surrounding unselected second texts and the first text 910 may be represented in the dashed lines. However, the example of displaying the text selected by the user to be distinguished from the unselected text on the display 140 is not limited to the above example.

After that, the display 140 deletes the unselected text from the screen. For example, when the user selects all the first text 910 and the second texts 940, the display 140 may continuously display the first text 910 and the second text 940 on the screen. When the user selects some of the second texts 940, the display 140 may delete unselected second texts and the first text 910 from the screen.

Figure 10:
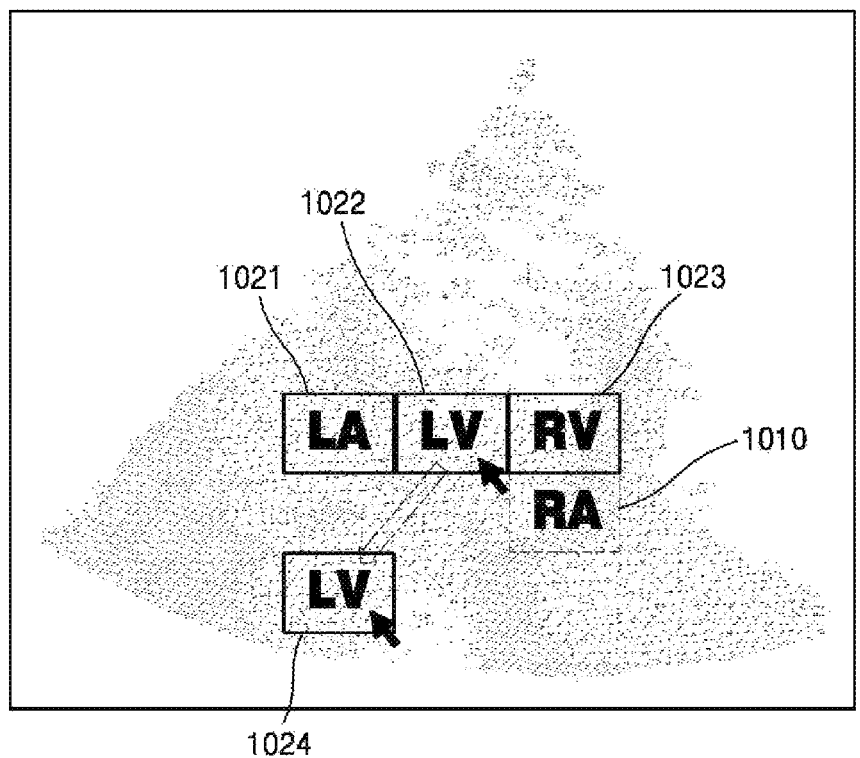
FIG. 10 is a diagram illustrating another example of displaying a first text and a second text together with an ultrasound image, according to an embodiment.

FIG. 10 is a diagram illustrating another example of displaying a first text 1020 and second texts 1021, 1022, and 1023 together with an ultrasound image 1010, according to an embodiment.

Referring to FIG. 10, the first text 1020 and the second texts 1021, 1022, and 1023 are displayed on the ultrasound image 1010. Here, the example of displaying the first text 1020 and the second texts 1021, 1022, and 1023 is the same as the above description provided with reference to FIG. 9.

In addition, the display 140 may adjust a location of displaying the second texts 1021, 1022, and 1023. For example, when the user adjusts the location of the second text 1022 displayed on the screen via the input unit 170, the display 140 may display the second text 1024 at an adjusted location.

In addition, the display 140 may display the second text 1024 at a location represented by the second text 1024 on the ultrasound image 1010, without receiving the user's input for adjusting the location. Here, an example of displaying the second text 1024 at the location represented by the second text 1024 on the ultrasound image 1010 by the display 140 is the same as the above description provided with reference to FIG. 8.

Also, as described above with reference to FIG. 7, the display 140 may adjust the location of displaying the second text 1024 based on the user input.

Figure 11:
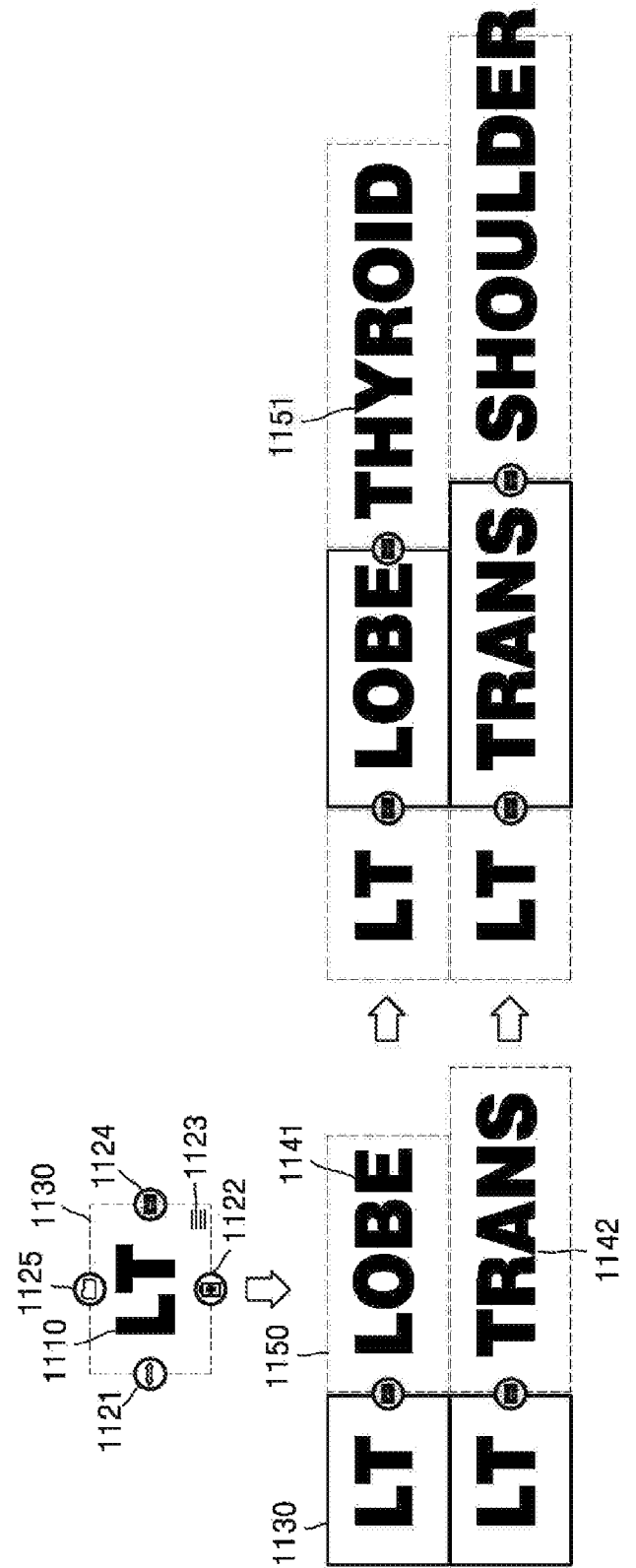
FIG. 11 is a diagram illustrating another example of displaying a first text and a second text, according to an embodiment.

FIG. 11 is a diagram illustrating another example of displaying a first text 1110 and second texts 1141 and 1142, according to an embodiment.

Referring to FIG. 11, the user may select a third icon 1124 from among a plurality of icons 1121, 1122, 1123, 1124, and 1125 displayed with the first text 1110. When the user selects the third icon 1124, the controller 120 generates the second texts 1141 and 1142. For example, when it is assumed that the third icon 1124 stands for terminologies regarding the first text and the first text 1110 is 'LT', the controller 120 may generate 'LOBE', 'TRANS', etc. as the second texts 1141 and 1142.

The display 140 may display the second texts 1141 and 1142 to be adjacent to sides of a polygon 1130 including the first text 1110. The display 140 may display the second texts 1141 and 1142 to be adjacent to the sides located at the directions represented respectively by the second texts 1141 and 1142 based on the location of the first text 1110, from among the sides of the polygon 1130. Here, the display 140 may output a predetermined polygon 1150 along with an outskirt of each of the second texts 1141 and 1142.

In addition, the user may select the third icon 1124 a plurality of times. For example, after displaying the second text 1141 'LOBE' when the user initially selects the third icon 1124, the user selects the third icon 1124 again to display a second text 1151, e.g., 'THYROID'. Here, the second text 1151 may be displayed adjacent to the second text 1141. The second texts 1141 and 1151 may be displayed sequentially in an order of utilization frequency, from among the texts stored in advance.

In a state where the first text 1110 and the second texts 1141 and 1151 are output, the user may select at least one of the first and second texts 1110, 1141, and 1151. For example, the user may select all the first text 1110 and the second texts 1141 and 1151 via the input unit 170, or may select at least one of the second texts 1141 and 1151. When the user finishes the selection, the display 140 may display the selected text to be distinguished from the unselected text. For example, in a case where all the first text 1110 and the second texts 1141 and 1151 are selected, the display 140 may represent all of polygons surrounding the first text 1110 and the second texts 1141 and 1151 by using solid lines. On the other hand, if some of the second texts 1141 and 1151 is only selected, the polygons surrounding the selected second texts may be represented by solid lines and the polygons surrounding unselected second texts and the first text 1110 may be represented by dashed lines. However, the example of displaying the text selected by the user to be distinguished from the unselected text on the display 140 is not limited to the above example.

After that, the display 140 deletes the unselected text from the screen. For example, when the user selects the second text 1141, the display 140 deletes the unselected second text 1151 and the first text 1110 from the screen.

Figure 12:
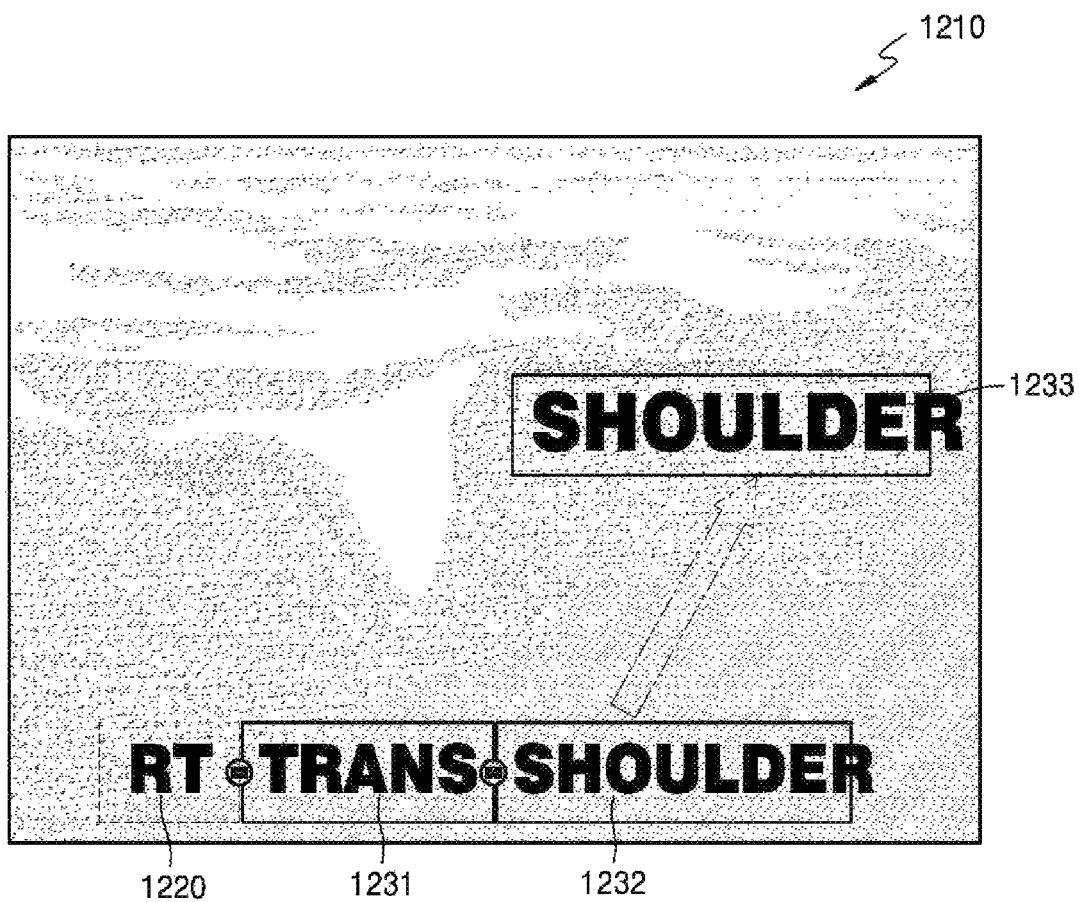
FIG. 12 is a diagram illustrating another example of displaying a first text and a second text together with an ultrasound image, according to an embodiment.

FIG. 12 is a diagram illustrating another example of displaying a first text 1220 and second texts 1231 and 1232 together with an ultrasound image 1210, according to an embodiment.

Referring to FIG. 12, the first text 1220 and the second texts 1231 and 1232 are displayed on the ultrasound image 1210. Here, the example of displaying the first text 1220 and the second texts 1231 and 1232 is the same as the above description provided with reference to FIG. 11.

In addition, the display 140 may adjust a location of displaying the second texts 1231 and 1232. For example, when the user adjusts the location of the second text 1232 displayed on the screen via the input unit 170, the display 140 may display the second text 1233 at an adjusted location.

In addition, the display 140 may display the second text 1233 at a location represented by the second text 1233 on the ultrasound image 1210, without receiving the user's input for adjusting the location. Here, an example of displaying the second text 1233 at the location represented by the second text 1233 on the ultrasound image 1210 by the display 140 is the same as the above description provided with reference to FIG. 8.

Also, as described above with reference to FIG. 7, the display 140 may adjust the location of displaying the second text 1233 based on the user input.

Figure 13:
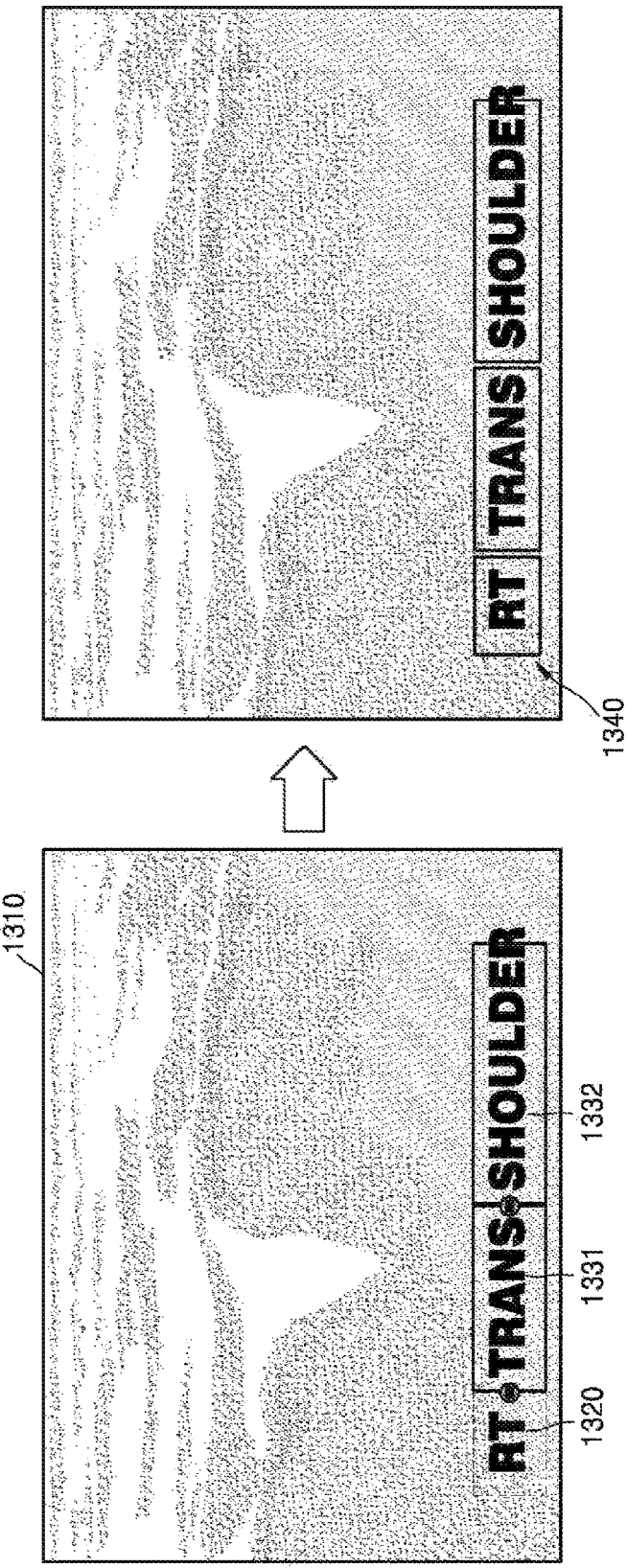
FIG. 13 is a diagram illustrating another example of displaying a first text and a second text together with an ultrasound image, according to an embodiment.

FIG. 13 is a diagram illustrating another example of displaying a first text 1320 and second texts 1331 and 1332 together with an ultrasound image 1310, according to an embodiment.

Referring to FIG. 13, the first text 1320 and the second texts 1331 and 1332 are displayed on the ultrasound image 1310. Here, in a case where the user selects all of the first text 1320 and the second texts 1331 and 1332 via the input unit 170, texts 1340 on the ultrasound image 1310 may not be deleted, but are connected to one another and displayed.

Figure 14:
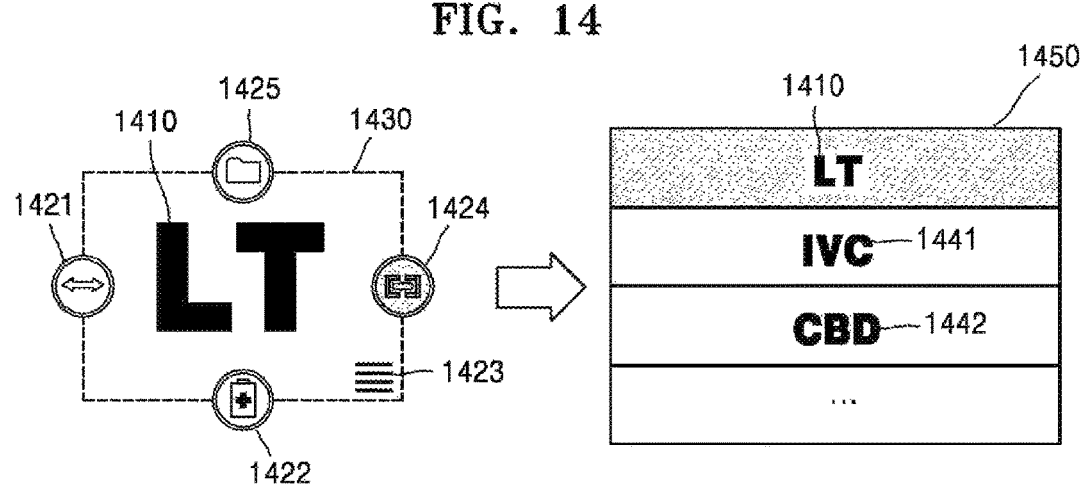
FIG. 14 is a diagram illustrating another example of displaying a first text and a second text, according to an embodiment.

FIG. 14 is a diagram illustrating another example of displaying a first text 1410 and second texts 1441 and 1442, according to an embodiment.

Referring to FIG. 14, the user may select a fourth icon 1422 from among a plurality of icons 1421, 1422, 1423, 1424, and 1425 displayed with the first text 1410. When the user selects the fourth icon 1422, the controller 120 generates the second texts 1441 and 1442. For example, when it is assumed that the fourth icon 1422 stands for medical terms, the controller 120 may generate 'IVC', 'CBD', and etc. as the second texts 1441 and 1442.

In addition, when the fourth icon 1422 is selected, the display 140 may output a pop-up window 1450 including the first text 1410 and the second texts 1441 and 1442.

FIG. 15 is a flowchart illustrating another example of a method of displaying an ultrasound image, according to an embodiment.

Referring to FIG. 15, the method of displaying an ultrasound image consists of processes that are processed in a time-serial manner in the ultrasound diagnosis apparatus 100, 100a, 100b, or 100c illustrated with reference to FIG. 1 and FIGS. 2A to 2C. Therefore, although omitted hereinafter, descriptions about the ultrasound diagnosis apparatus 100, 100a, 100b, or 100c illustrated with reference to FIGS. 1 and 2A to 2C provided above are also applied to the method of displaying the ultrasound image illustrated with reference to FIG. 15.

Operations 1510 to 1550 of FIG. 15 are equal to operations 310 to 350 of FIG. 3. Therefore, detailed descriptions about operations 1510 to 1550 of FIG. 15 are omitted.

In operation 1560, the display 140 may adjust a location of displaying at least one second text. For example, when the user adjusts the location of the second text displayed on the screen via the input unit 170, the display 140 may display the second text at an adjusted location.

As described above, the user may rapidly and conveniently select the text to be displayed on the ultrasound image, from among the texts stored in advance. In addition, blocking of the ultrasound image when the texts stored in advance in the ultrasound diagnosis apparatus are displayed with the ultrasound image may be prevented. Also, taking a lot of time for the user to search the texts stored in the ultrasound diagnosis apparatus in advance for a desired text may be prevented.

The above methods according to the embodiments can be recorded in programs that can be executed on a computer and be implemented through general purpose digital computers which can run the programs using a non-transitory computer-readable recording medium. Data structures described in the above methods can also be recorded on a non-transitory computer-readable medium in a variety of ways, with examples of the medium including recording media, such as magnetic storage media (e.g., ROM, RAM, USB, floppy disks, hard disks, etc.) and optical recording media (e.g., CD-ROMs or DVDs).

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of outputting an ultrasound image, the method comprising:
    displaying an ultrasound image representing an object;
    generating a first text representing information about a region of interest included in the object and a plurality of icons related to the first text;
    displaying the first text and the plurality of icons on a first region of the ultrasound image, each of the plurality of icons being displayed around the first text;
    generating at least one second text representing information about the region of interest included in the object, in response to selection of a first icon from among the plurality of icons displayed on the first region of the ultrasound image; and
    displaying the at least one second text on a second region of the ultrasound image, the second region being related to information represented by the at least one second text;
    wherein the plurality of icons comprise an icon for obtaining a text representing names of organs relating to the region of interest, an icon for obtaining a text representing terms used in connection with the first text, an icon for obtaining a text representing medical terms, and an icon for obtaining a text opposite the first text.

2. The method of claim 1, wherein the displaying of the at least one second text comprises displaying the at least one second text adjacent to a corner of a polygon including the first text.

3. The method of claim 2, wherein the corner exists at a location represented by the at least one second text, based on a location of the first text, from among sides of the polygon.

4. The method of claim 1, wherein each of the plurality of icons is displayed adjacent to a corner of a polygon including the first text.

5. The method of claim 1, wherein the generating of the at least one second text comprises sequentially generating second texts that are different from one another when the first icon is selected a plurality of times.

6. The method of claim 5, wherein the second texts different from one another are selected in an order of utilization frequency from among texts stored in advance.

7. The method of claim 1, further comprising adjusting a location where the at least one second text is displayed.

8. The method of claim 1, wherein the first text comprises a text input by a user.

9. The method of claim 1, further comprising obtaining information about the region of interest included in the object by analyzing the ultrasound image,
    wherein the first text comprises a text selected from among texts stored in advance based on the information about the region of interest.

10. A non-transitory computer-readable recording medium having recorded thereon a program, which when executed by a computer, performs the method of claim 1.

11. An ultrasound diagnosis apparatus comprising:
    a probe comprising ultrasound transducers configured to irradiate ultrasound signals to an object and to receive echo signals corresponding to the ultrasound signals; and
    a processor configured to:
        control a display to display an ultrasound image of the object based on the received echo signals;
        generate a first text representing information about a region of interest included in the object and a plurality of icons related to the first text;
        control the display to display the first text and the plurality of icons on a first region of the ultrasound image, each of the plurality of icons being displayed around the first text;
        generate at least one second text representing information about the region of interest included in the object, in response to selection of a first icon from among the plurality of icons displayed on the first region of the ultrasound image; and
        control the display to display the at least one second text on a second region of the ultrasound image, the second region being related relating to information represented by the at least one second text;
    wherein the plurality of icons include an icon for obtaining a text representing names of organs relating to the region of interest, an icon for obtaining a text representing terms used in connection with the first text, an icon for obtaining a text representing medical terms, and an icon for obtaining a text opposite the first text.

12. The ultrasound diagnosis apparatus of claim 11, wherein the processor is further configured to control the display to display the at least one second text adjacent to a corner of a polygon including the first text.

13. The ultrasound diagnosis apparatus of claim 12, wherein the corner exists at a location represented by the at least one second text, based on a location of the first text, from among sides of the polygon.

14. The ultrasound diagnosis apparatus of claim 11, wherein each of the plurality of icons is displayed adjacent to a corner of a polygon including the first text.

15. The ultrasound diagnosis apparatus of claim 11, wherein the processor is further configured to sequentially generate second texts that are different from one another when the first icon is selected a plurality of times.

16. The ultrasound diagnosis apparatus of claim 15, wherein the second texts that are different from one another are selected in an order of utilization frequency from among the texts stored in advance.

17. The ultrasound diagnosis apparatus of claim 11, wherein the processor is further configured to control the display to display the at least one second text after adjusting a location where the at least one second text is displayed.

18. The ultrasound diagnosis apparatus of claim 11, wherein the first text comprises a text input by a user.

19. The ultrasound diagnosis apparatus of claim 11, wherein the processor is further configured to obtain information about the region of interest included in the object by analyzing the ultrasound image, and the first text comprises a text selected from among texts stored in advance based on the information about the region of interest.

* * * * *